(12) United States Patent
Puscas et al.

(10) Patent No.: US 6,326,161 B1
(45) Date of Patent: Dec. 4, 2001

(54) RAPID MOTOR FOR CANCER DIAGNOSIS

(76) Inventors: Ioan Puscas; Carmen Iuliana Puscas, both of Cetatii 10, Simleu Silvaniei Salei R-4775 (RO); Marcela Coltau, Building M-1, Partizanilor 14, Simleu Silvaniei, Salei R-4775 (RO); Gabriela Domuta, Gh. Lazar L-21/4, Simleu Silvaniei Salei (RO), R-4775; Michael Bajcan, Klinik Wilkenberg, Meinerzhagen (DE), D-58540

( * ) Notice: Subject to any disclaimer, the term of this patent is extended or adjusted under 35 U.S.C. 154(b) by 0 days.

(21) Appl. No.: 09/381,319

(22) PCT Filed: Mar. 13, 1998

(86) PCT No.: PCT/EP98/01465
§ 371 Date: Jan. 12, 2000
§ 102(e) Date: Jan. 12, 2000

(87) PCT Pub. No.: WO98/41649
PCT Pub. Date: Sep. 24, 1998

(30) Foreign Application Priority Data

Mar. 17, 1997 (RO) ................................. 97-00502

(51) Int. Cl.⁷ ............................ C12Q 1/34; C12Q 1/00; G01N 33/48
(52) U.S. Cl. .................................. 435/18; 435/4; 436/64
(58) Field of Search ............................ 435/18, 4; 436/64

(56) References Cited

U.S. PATENT DOCUMENTS 5,589,579 * 12/1996 Torczynski et al. .

OTHER PUBLICATIONS

WO 9602552A1. Torczynski et al. (02–1996). Lung cancer marker.*
Franz et al. (1994). Tumor necrosis factor–a induces the expression of carbonic anhydrase II in pancreatic adenocarcinoma cells. Biochemical and Biophysical Research Communications, 205(3), pp. 1815–1821.*
Medline abstract (Acc No. 97188307). Yokoyama et al. (Mar. 1997). The potential role of fecal carbonic anhydrase II in screening for colorectal cancer. American Surgeon, 63(3), pp. 243–246.*

* cited by examiner

*Primary Examiner*—Ralph Gitomer
*Assistant Examiner*—Mahreen Chaudhry
(74) *Attorney, Agent, or Firm*—John S. Child, Jr.

(57) ABSTRACT

A rapid method for cancer diagnosis which is suitable to detect the presence of a carcinogenic process in a subject in the a symptomatic phase or the early phase. Also disclosed is an activator compound of carbonic anhydrase II, i.e., a tumor marker, which is present in the serum of subjects having cancer, a method of treating cancer, and a kit for performing the method for cancer diagnosis.

16 Claims, No Drawings

RAPID MOTOR FOR CANCER DIAGNOSIS

BACKGROUND OF THE INVENTION

1. Field of the Invention

The present invention relates to a rapid method for cancer diagnosis which is suitable to detect the presence of a carcinogenic process in a subject in the asymptomatic phase or the early phase. The present invention further relates to an activator compound of carbonic anhydrase II, i.e., a tumor marker, which is present in the serum of subjects having cancer; to a method for treating cancer, which method comprises detecting cancer in the patient in the asymptomatic phase or in early stage by said method for cancer diagnosis; and to a kit for performing said method for cancer diagnosis. The method for cancer diagnosis of the invention is based on an effect of cancer patients serum on the activity of purified carbonic anhydrase II. It was found that the activity of purified carbonic anhydrase II is significantly increased by the addition of a suitable amount of the serum of cancer patients. On the other hand, neither the serum of healthy volunteers nor the serum of patients having other diseases except cancer show a similar effect.

2. Description of the Related Art

Carbonic anhydrase is a zinc-enzyme discovered by Meldrum et al. in 1932 (Meldrum N. U., Roughton J. W.: Carbonic Anhydrase: Its preparation and properties, J. Physiol. (London), 1933, 80, 113–142). This enzyme is located in red blood cells and in other cells of the organism participates in the maintenance of the acid-base equilibrium (Maren T. H.: Carbonic Anhydrase, Physiological Reviews 1967, 47, 585–782; Hewett-Emmett D., Hopkins P. J., Tashian R. E., Czelusniak J. Origins and molecular evolution of the carbonic anhydrase isozymes, Ann. N.Y. Acad. Sci. 1984, 429, 338–358). Eight distinct isozymes of carbonic anhydrase are known in vertebrates (designated from I to VIII), which have different physiological functions and are involved in: gastric acid secretion, aqueous humour and cephalo-rachidian fluid formation, pancreatic bicarbonat secretion, intermediary metabolism, calcification, etc.

Applicants' previous research work demonstrated that carbonic anhydrase specific inhibitors (acetazolamide, ethoxzolamide, benzthiazol-2-sulphonamide) administered orally in the usual therapeutical doses reduce gastric acid secretion and lead to disappearance of ulcer pain and to endoscopic healing of gastroduodenal ulcers within a very short time (I. Puscas et al.: Les inhibiteurs de I'anhydrase carbonique dans le traitement de I'ulcere gastrique et duodenal, Archive Frangaises des Maladies de I'Appareil Digestif, Paris, 1976, 65:577–583; I. Puscas: Treatment of gastroduodenal ulcers with carbonic anhydrase inhibitors, Ann. New York Acad. of Sciences, 1984, 587–591; I. Puscas: Carbonic anhydrase inhibitors in the treatment of gastric and duodenal ulcers, in: New Pharmacology of Ulcer Disease, S. Szabo, Gy. Mozsik (Editors) Elsevier Publ. House, New York, USA,164–178, 1987; I. Puscas: Farmacologia Clinica da Ulcera Peptica, In: Aparelho Digestivo, Clinica e Cirurgia, Julio Coelho (Ed) MEDSI Publ. House, Rio de Janeiro, The 1st Edition in 1990,The 2nd Edition in 1996,1704–1734; I. Puscas: Avaliacao do paciente com doenca do estomago e duodeno, In: Aparelho Digestivo. Clinica e Cirurgia, Julio Coelho(Ed.), MEDSI Publ. House, Rio de Janeiro, Brasil, The 1st Edition in 1990, The 2nd Edition in 1996, 173–179).

Further research of applicants has shown that histamine, gastrin and acetylcholine—major stimulators of gastric acid secretion—directly activate carbonic anhydrase II and IV in gastric mucosa (I. Puscas: New concepts concerning the mechanism of stimulation of gastric acid secretion by histamine. VIth World Congress of Gastroenterology, Madrid, 1978, 213; I. Puscas: Direct activation by histamine of the carbonic anhydrase in the human gastric mucosa, Rev. Roum. Biochim.,1979, 4:317–320). Applicants' studies have also proved that the isozyme I of carbonic anhydrase which is located in red blood cells and in vascular walls is involved in the processes of vascular modulation (I. Puscas et al.: Inhibition of carbonic anhydrase by nitric oxide. Arzneimittel—Forschung/Drug Research, 1995, 8: 846–848; I. Puscas et al.: Prostaglandins having vasodilating effects inhibit carbonic anhydrase while leukotriens $B_4$ and $C_4$ increase carbonic anhydrase activity. Int. J. Clin. Pharmacol Therapeutics, 1995, 32, 3: 176–181; I. Puscas et al.: Isosorbide nitrates, nitroglycerine and sodium nitroprusside induce vasodilation, concomitantly inhibiting down to abolishment carbonic anhydrase I in erythrocytes. American Journal of Hypertension, 1997, 10 (1), 124–128), The izozyme II of carbonic anhydrase—located in the red blood cells and in the secretory cells—modulates the secretory processes in the organism (I. Puscas et al.: World Congress of Gastroenterology, Los Angeles, October 1994: 1329–32; 1366–81; I. Puscas et al.: Nonsteroidal anti-inflammatory drugs activate carbonic anhydrase by a direct mechanism of action. J. Pharmacol. Exp. Therap., USA, 1996,277, 3:1146–1148).

Applicants' results lead to postulation of a new theory for the signal transmission within the cell: The pH Theory. According to this theory, the stimuli or the primary messengers which produce vasculary and secretory modifications act by a dual mechanism: both on cellular membrane specific receptors and directly on bound-membrane carbonic anhydrase. This enzyme by its activation or inhibition assures an adequate pH for the stimulus-receptor complex formation in order to transmit the information to cellular effector. By this way through the pH modifications initiated by carbonic anhydrase this enzyme is involved in the modulation of physiological and pathological processes in the organism as well as in carcinogenesis (I. Puscas et al.: Carbonic anhydrase and modulation of physiologic and pathological processes in the organism, I. Puscas—(Editor), Helicon Publishing House Timisoara, Romania, 1994, the Romanian version p.155–205 and 577–585, and the English version p. 147–197 and 551–559; I. Puscas: Carbonic anhydrase—a modulator of physiologic and pathologic processes in the organism: The pH Theory. The 4th International Conference on the Carbonic Anhydrases, July 1995, University of Oxford, England; I. Puscas: Carbonic anhydrase modulating physiological and pathological processes in organism. The pH theory. The Medical Novelty (Noutatea Medicala), Bucharest, Romania, 1997, 3:5–15)

The past few years have witnessed remarkable progress in understanding the biologic and biochemical bases for cancer. Cancer is a disease characterized by the uncontrolled growth of abnormal cells that spread from the anatomic site of origin to other tissues. This metastatic process involves a variety of cellular events taking place before any tumor cell gives rise to a metastatic colony. This spread, if uncontrolled, is the primary cause for the fatal outcome of cancer diseases. However, many cancers can be cured if they are detected early and treated promptly; others can be controlled for many years with a variety of treatment approaches.

Applicants' in vitro and in vivo studies have proved that carcinogenic substances reduce carbonic anhydrase II and superoxide dismutase activity and anticarcinogenic ones increase these enzymes' activity. (I. Puscas et al.: Relation between carbonic anhydrase I, CA II, non-steroidal anti-inflammatory drugs and some carcinogenic substances, Digestive Disease Week, San Diego, Calif., May 1995, 0643; I. Puscas et al.: The values of superoxid dismutase in patients with gastric cancer as compared to controls, Digestive Disease Week, San Francisco, Calif., May 1996, 0798; I. Puscas et al.: Anticancer chemotherapy increases red cell and gastric mucosa carbonic anhydrase activity. In vivo studies. Digestive Disease Week, San Francisco, Calif., May 1996, 0797). Other recent studies of applicants—performed with patients having different forms of cancer (histologically and computed tomography confirmed)—have shown that red blood cell carbonic anhydrase II and superoxide dismutase activity are weak in all patients, as compared to control group constituted by healthy volunteers (I. Puscas et al.: The effect of benzpyrene and cyclophosphamide on superoxid dismutase and carbonic anhydrase activity in gastric carcinoma patients as compared to controls. The First Forum of Gastroenterology, "Banat-Crisana", Timisoara, Romania, October 1996).

Up to the present, in many cases early detection of tumors and careful monitoring of the disease is conceivable by using tumor markers which are the biochermical indicators for the presence of a neoplastic proliferation and that can be detected in serum, plasma, or other body fluids. The main utility of tumor markers such as carcinoembryonic antigen (CEA), tumor necrosis factor (TNF-$\alpha$ and $\beta$), sialic acid, prostate specific antigen (PSA), etc., has been in determining the response to therapy, the detection of residual disease or relapse. Until today no tumor marker has shown to be specific; virtually most of them are present at low levels in the normal physiological state or in non-neoplastic disease. Thus, these markers are not applicable in a general screening test for cancer.

In order to eliminate the major disadvantages of tumoral markers this invention is concerned in establishing a rapid method of screening for cancer in its asymptomatic stage, or their confirmation in the symptomatical phase. This early detection of cancer disease allows an efficient surgical or drug therapy along with other usual method utilized for tumor localization.

Applicant has now found that the activity of purified carbonic anhydrase II is significantly activated by the serum of cancer patients and that such activation is not observed with serum of healthy persons or serum of patients having other diseases but cancer. Starting from these observations, applicants found that by testing the effect of blood serum on the activity of purified carbonic anhydrase II is possible to diagnose any type of cancer, even those in early stages.

SUMMARY OF THE INVENTION

Thus, the present invention provides
(1) a method for cancer diagnosis comprising
  (a) preparing a first reaction mixture by combining a diluted blood serum sample of the subject to be tested and a solution of purified carbonic anhydrase II;
  (b) determining the activity of the carbonic anhydrase II in the first reaction mixture;
  (c) determining the activity of carbonic anhydrase II in a second reaction mixture containing all constituents of the first reaction mixture except the blood serum; and
  (d) assessing the degree of activation of carbonic anhydrase II in step (b) relative to step (c);
(2) a tumor marker present in the serum of subjects having cancer, said tumor marker activating carbonic anhydrase at concentrations of 1 $\mu$M or below;

(3) a method for treating cancer, which method comprises detecting the cancer process in a patient in the asymptomatic phase or in early stage by a method for cancer diagnosis as defined in (1) above; and
(4) a kit for performing the method for cancer diagnosis as defined in (1) above, which kit comprises a composition containing carbonic anhydrase II.

DETAILED DESCRIPTION OF THE INVENTION

The method for cancer diagnosis of the present invention is an in vitro method and preferred subjects to be tested are human beings.

In a preferred embodiment of the method for cancer diagnosis the diluted blood serum contains from 0.1 to 50 vol. %, preferably from 1 to 10 vol. % of blood serum. The diluent for the diluted blood serum sample is selected from water and aqueous organic solvents, e.g., aqueous mixtures containing 0.1 to 50 vol. %, preferably 1 to 15 vol. % of one or more organic solvents, which diluents may optionally contain a buffer and/or organic or inorganic salts. Suitable organic solvents include lower alcohols, such as methanol, ethanol, propanol, isopropanol and butanol, ketones, such as aceton and butanon, diol and triol compounds, such as ethylenglycol 1,3-propanediol and glycerin, and ethers, such as diethylether, diethylenglycol, and 2-methoxyethanol. Suitable buffers include HEPES, DIPSO, TAPSO, TES and MOPS and suitable organic or inorganic salts include $Na_2SO_4$ and $K_2SO_4$.

The concentration of the carbonic anhydrase II in the solution of purified carbonic anhydrase II ranges from 0.01 nM to 0.1 mM, preferably 1.0 nM to 1.0 $\mu$M. Suitable solvents of said solution are selected from water and aqueous organic solvents, which solvents may further contain a buffer, inorganic or organic salts, and/or one or more indicator (s). With regard to the organic solvents, buffers and organic and inorganic salts it is referred to the diluted blood serum sample defined above. Suitable indicators include p-nitrophenol, phenol red and nitro-blue tetrazolium.

According to the invention of the present application it is preferred that the diluted blood serum sample and the solution of purified carbonic anhydrase are combined at a ratio of 100:1 to 1:100, preferably at a ratio of 10:1 to 1:10, and more preferably at a ratio of 1:1.

In a preferred embodiment the first reaction mixture contains from 0.05 to 25 vol. %, preferably from 0.5 to 5 vol. % of blood serum. It is understood that an activation of 100% or higher in the first reaction mixture—whereby said first reaction mixture contains 25 vol. % or less, preferably 5 vol. % or less serum—relative to the carbonic anhydrase II activity of the second reaction mixture (viz. the activity of carbonic anhydrase in the first reaction mixture being at least twice as high as in the second reaction mixture), indicates the presence of a carcinogenic process of the subject.

In a further preferred embodiment of the method of the present invention the diluted blood serum sample is an aqueous solution containing 10 vol. % serum, the solution of purified carbonic anhydrase II is an aqueous buffer solution containing from 1.0 to 10 $\mu$M carbonic anhydrase II, and the first reaction mixture contains the diluted blood serum sample and the solution of purified carbonic anhydrase II at a ratio of 1:1.

The carbonic anhydrase II activity can be determined using one of the known methods, e.g., as described in the specialty literature cited hereinbefore. In a preferred embodiment of the method of the present invention, the carbonic anhydrase activity is determined by the stop-flow method (Khalifah R. G.: The carbon dioxide hydration activity of carbonic anhydrase: stop-flow kinetic studies on the native human isozymes B and C, J. Biol. Chem., 1971, 246:2561–2573). This method comprises measuring the enzymatic activity on $CO_2$ hydration. The $CO_2$ hydration is followed by a colorimetric method based on the change of the pH. The time in which the pH of the reagent mixture decreases from its initial value of 7.5 to its final value of 6.5 is measured. The reaction is followed spectrophotometrically at 400 nm wave length, using a rapid kinetic spectrophotometer HI-TECH SF-51MX (England), equipped with a mixing unit and a system of two syringes which supply the reagents. The reagent supply in the reaction cuvet is ensured by two separate paths: syringe one introduces the reaction mixture made up of enzyme-buffer (i.e., the first or second reaction mixture), while a second syringe introduces the substrate solution, which is an aqueous $CO_2$ solution having a $CO_2$ content of 5 to 50 mM, preferably 15 nM. The reagents are mixed on entering the reaction cuvet whereby the reaction and its monitoring starts. The signal transmitted by photomultiplier from the mixing chamber is received and visualized by a computer equipped with a mathematical coprocessor and a kinetic soft RKBIN IS-1.

Detection of carbonic anhydrase activity might also be assessed by other methods such as:

Methods based on changes of pH (Philpot F. J. et at. A modified colorimetric estimation of carbonic anhydrase, Biochem. J., 1936; 30:2192–94; Kernohan J. K. et al.: The activity of concentrated solutions of carbonic anhydrase, Biochem.Biophys Acta, 1963; 67: 31–41; Maren T. H.: Carbonic anhydrase: chemistry, physiology and inhibition. Physiol.Rev.1967, 47:595–781; Wilbur K. M. &Anderson N. O. Electrometric and calorimetric determination of carbonic anhydrase. J.Biol.Chem.1948, 176: 147–153). Said method is based on the measurement of the $H^+$ production and consumption and can be carried out by a) pH indicators in which case the $H^+$ production is visualized by change of color of an indicator or by b) pH electrodes in which case the $H^+$ production and consumption is measured with pH electrodes.

Methods based on changes of the $CO_2$ concentration or the $pCO_2$, which are based on the measurement of the $CO_2$ production or the consumption of the reversible $CO_2$—$HCO^{\rightleftharpoons}_3$ reaction by a) the gas manometric technique (Meldrum N. U., Roughton F. J. W., J. Physiol, London, 1933, 80:113–142; Roughton F. J. W. et al. Biochem J., 1946, 40:319–390) or by b) $pCO_2$ electrodes (Holland R. A. B. et al. J. Physiol., London, 1975, 228: 1589–1596; Klocke R. A., J. Appl. Physiol., 1976, 40: 707–714).

Methods based on changes of the reaction temperature, which are based on the measurement of the rapid initial increase in temperature caused by the reaction, an assessment being achieved with an apparatus equipped with thermocouples (Kernohan J. C. et al., J. Physiol., London, 1968, 197:345–361).

Methods with labelled isotopes (tracers) such as $^{18}O$ (Silverman D. N., Methods Enzymol.1982, 87:732–752).

Methods applying nuclear magnetic resonance (NMR) with $^{13}C$. (Simonsson I. et al., Eur. J.Biochem. 1979, 93:409–417).

Relaxation methods in which the $HCO_3$—$CO_2$ solution equilibrium suddenly modifies its physical properties, for instance its electrical field, pressure or temperature with consecutive modification of the chemical equilibrium state (Eigen M. et al., Z. Physik. Chem. NF, 1961, 30:130–136).

Imunohistochemical methods which are based on cobalt trapping of $CO_2$ produced by carbonic anhydrase, and which served to localize carbonic anhydrase in a number of sites of the body (Hansson H. P. J.: Histochemical demonstration of carbonic anhydrase activity, Histochemie, 1967,11: 112–128; Lonnerholm G.: Histochemical demonstration of carbonic anhydrase activity in the human kidney, Acta Physiol. Scand., 1973, 88:455–468).

Fluorometric methods (Shingles R., Moroney J. V.: Measurement of carbonic anhydrase activity using a sensitive fluorometric assay, Analytical Biochemistry, 1997, 252, 1:190–198).

Methods using other substrates for carbonic anhydrase assessment such as p-nitrophenyl acetate (Schneider F. et al.: Uber die Reaktion von Carbonathydrolyase mit p-Nitrophenylacetat, Z. Physiol. Chem., 1963, 334:279–282).

As set forth above, an activation value of 100% or higher in the first reaction mixture (which contains 25 vol. % or less, preferably 5 vol. % or less serum) relative to the carbonic anhydrase II activity of the second reaction mixture indicates the presence of a carcinogenic process. Moreover, it was found by applicants that a weaker activation of carbonic anhydrase II was achieved by using the serum of initial stages cancer patients (regardless of the localization of the cancer). Thus, the method of the invention is further suitable to determine the stage of the cancer process in patients (via comparison of the degree of activation of carbonic anhydrase II), as compared to the serum of patients activation in a more advanced stages. Nevertheless in all cases with initial stages cancer patients carbonic anhydrase II activation (with the first reaction mixtures having 5 vol. % serum) exceeded 100% and the activation produced by the advanced stage patients serum reached 400% or even more.

The method of the present invention possesses the following advantages:

1. It permits the screening of carcinomas in the asymptomatic phase, respectively in early stages which carcinomas are undetectable by conventional methods.
2. It is performed using a small quantity of blood serum.
3. It is highly sensitive and the assessments are reproducible.
4. It is economically feasable because of the low prices of the required reagents.

Starting from the above results—concerning the activating effect of the serum of cancer patients on carbonic anhydrase II—it was tried to identify some responsible factors (i.e., tumor markers) for carbonic anhydrase II activation in the serum of said cancer patients. Thus, it was shown that tumor necrosis factor $\alpha$ and $\beta$, carcinoembryonic antigen, sialic acid and $\alpha_1$-antichymothrypsine are powerful activators of carbonic anhydrase II. Applicants' studies have also proved that serum gastrin levels are high in 80% of the cancer patients as compared to healthy volunteers serum. Thus, this one might be among the serum endogenous activators of carbonic anhydrase II.

The tumor markers according to the present invention activate carbonic anhydrase II even at concentrations below 1 $\mu$M, in particular even at concentrations of 1 nM or below, and even at concentrations of 1 pM or below. Preferable tumor markers include tumor necrosis factor $\alpha$ and $\beta$, carcinoembryonic antigen (CEA), sialic acid, $\alpha_1$-antichymothrypsine and sp $185^{Her2}$ oncoprotein.

The tumor markers of the present invention can be used as standard solutions for quantitating the detected activation percentage, in particular for determining the stage of the cancer process.

The method for treating cancer according to the present invention, which comprises detecting the cancer process in a patient in the asymptomatic phase or in early stage as defined hereinbefore, is suitable to treat any kind of cancers in patients. The method for cancer diagnosis according to the present invention may therefore be combined with any kind of therapeutic treatment (e.g., surgical or chemotherapeutic). The detection in initial stages of the cancer process increases the chances of curing of the cancer process.

The kit for performing the method for cancer according to the present invention comprises a composition containing carbonic anhydrase II. Said composition may be in the dry state or be a solution. For further ingredients of the composition and the amount of carbonic anhydrase II in the composition it is referred to the discussion of the compounds of the first reaction mixture hereinbefore.

The kit may further comprise compositions containing a buffer, e.g., buffer solutions, compositions containing an indicator substance, and compositions containing one or more tumor markers, wherein the buffer, indicator and tumor marker are as defined herein before.

The present invention is described in more detail by means of the following non-limiting examples.

EXAMPLES

Reagents p-nitrophenol—as color indicator—was used at a concentration of 0.2 mM; pH=7.5; temperature 20–25° C.=room temperature (hereinafter ..r.t.")

HEPES buffer was used at a concentration of 20 mM; pH=7.5; r.t.

a stock solution of purified carbonic anhydrase II (obtained from SIGMA Diesenhofen, Germany) was used at concentration of $3.44 \times 10^{-6}$ M; pH=7.5; r.t.

a $CO_2$ solution at a concentration of 15 mM (as substrate) was obtained by bubbling $CO_2$ in bidistilled water to saturation.

$Na_2SO_4$—at a concentration of 0.1 M—was used to keep up constant ionic strength.

The assessment of purified carbonic anhydrase II activity was performed by measuring the time in which the $CO_2$ hydration in the presence of said enzyme occured. The measurement stated at the moment when the reaction began (when the absorbance of the reaction mixture absorbance was of 3 units) until the end of reaction (when the absorbance of the reaction mixture absorbance turned zero). The absorbance values were depicted in a reaction curve.

The reaction cuvet comprised two syringes containing:

Syringe I: 1 ml mixture of: 0.8 ml buffer+indicator+0.1 ml CA II solution ($3.44 \times 10^{-6}$ M)+0.1 ml $H_2O$.

Syringe II: 1 ml $CO_2$ solution (15 mM).

Reagent injection and carbonic anhydrase activity measurements were performed as described above. The reaction time measured in this way was noted as T.

The activity of carbonic anhydrase was assessed by the formula:

$$A = \frac{T_0 - T}{T} \quad [EU/ml]$$

where $T_0$ represents the uncatalyzed reaction time;

and T represents the catalyzed reaction time (in the presence of CA II).

The measurement of carbonic anhydrase II activity in the presence of serum according to the method of the present invention was performed as follows:

Example 1

5 ml venous blood was collected from a patient diagnosed with gastric cancer. The blood was kept 30 minutes in a thermostat and was then centrifuged for 5 minutes at 4000 rpm. After centrifugation 2 ml of serum were removed and three dilutions of 1/10, 1/50 and 1/100 in bidistilled water were made as follows: from 0.5 ml serum+4.5 ml $H_2O$ a 1/10 dilution was obtained; taking 1 ml serum from the dilution of 1/10 and adding 4 ml $H_2O$ the 1/50 dilution was obtained; finally, taking 1 ml serum from the dilution of 1/50+4 ml $H_2O$ the 1/100 dilution was obtained.

The first step was the measurement of uncatalyzed reaction time, i.e., the determination of the reaction time between: 0.8 ml buffer+indicator and+$CO_2$ solution. The time measured in this way was marked as $T_0$ and it was of 6.5 s.

The second step was the measurement of the reaction time of $CO_2$ solution with 0.1 ml purified carbonic anhydrase II ($3.44 \times 10^{-6}$ M) within 0.8 ml buffer+indicator and+0.1 ml $H_2O$. The time measured in this way was noted as T and it was of 3.25 s.

The activity of purified carbonic anhydrase II in the presence of $H_2O$ was obtained from the following formula:

$$A = \frac{T_0 - T}{T} = \frac{6.5s - 3.25s}{3.25s} = 1,00 \quad [EU/ml]$$

The third step: 1/100, 1/50 and 1/10 serum dilutions were each added, in volumetric ratio of 1:1 to 0.1 ml to a purified carbonic anhydrase II solution ($3,44 \times 10^{-6}$ M) in 0.8 ml HEPES buffer (20 mM)+indicator (p-nitrofenol 0,2 mM). Each mixture reaction time noted as $T_1, T_2, T_3$ was measured in the presence of $CO_2$. These values ($T_1, T_2, T_3$) represent the interval of time in which each reaction mixture absorbance fell to zero.

The following values were obtained:

$T_1$=1.679 s—for the 1/100 dilution;

$T_2$=1.264 s—for the 1/50 dilution;

$T_3$=0.874 s—for the 1/10 dilution;

The carbonic anhydrase II activity in the presence of serum were calculated as follows:

$$A_1 = \frac{T_0 - T_1}{T_1} = \frac{6.5s - 1.679s}{1.679s}$$

$$= 2.871 \quad [EU/ml] - \text{in the serum of 1/100 dilution;}$$

$$A_2 = \frac{T_0 - T_2}{T_2} = \frac{6.5s - 1.264s}{1.264s}$$

$$= 4.142 \quad [EU/ml] - \text{in the serum of 1/50 dilution;}$$

$$A_3 = \frac{T_0 - T_3}{T_3} = \frac{6.5s - 0.874s}{0.874s}$$

$$= 6.435 \quad [EU/ml] - \text{in the serum of 1/10 dilution;}$$

The activation percentages of the serum dilutions were calculated as follows:

$$\frac{A_1 - A}{A} \times 100 = \frac{2.871 - 1.00}{1.00} \times 100$$

$$= 187\% - \text{in the serum of 1/100 dilution;}$$

$$\frac{A_2 - A}{A} \times 100 = \frac{4.142 - 1.00}{1.00} \times 100$$

$$= 314\% - \text{in the serum of 1/50 dilution;}$$

-continued $$\frac{A_3 - A}{A} \times 100 = \frac{6.435 - 1.00}{1.00} \times 100$$

$$= 543\% - \text{in the serum of 1/10 dilution;}$$

Example 2

5 ml venous blood were collected from a patient diagnosed with pulmonary cancer and were processed in Example 1.
The first step: $T_0 32$ 6.40 s
The second step: $T=3.20$ s; $A=1.00$ [EU/ml]
The third step:
$T_1=2.143$ s (1/100 dilution); $A_1=1.986$ [EU/ml]; activation 98%;
$T_2=1.449$ s (1/50 dilution); $A_2=3.415$ [EU/ml]; activation 241%;
$T_3=1.125$ s (1/10 dilution); $A_3=4.686$ [EU/ml]; activation 368%.

Example 3

5 ml venous blood were collected from a patient diagnosed with brest cancer and were processed as in Example 1.
The first step: $T_0=6.35$ s;
The second step: $T=3.175$ s; $A=1,00$ [EU/ml];
The third step:
$T_1=2.201$ s (1/100 dilution); $A_1=1.885$ [EU/ml]; activation 88%;
$T_2=1.545$ s (1/50 dilution); $A_2=3.108$ [EU/ml]; activation 211%;
$T_3=1.170$ s (1/10 dilution); $A_3=4.425$ [EU/ml]; activation 342%;

Example 4

5 ml venous blood were collected from a patient diagnosed with ovarian cancer and were processed as in Example 1.
The first step: $T_0=6.52$ s;
The second step: $T=3.26$ s; $A=1,00$ [EU/ml];
The third step:
$T_1=2.330$ s (1/100 dilution);=$A_1=1.798$ [EU/ml]; activation 80%;
$T_2=1.664$ s (1/50 dilution); $A_2=2.917$ [EU/ml]; activation 192%;
$T_3=1.338$ s (1/10 dilution); $A_3=3.870$ [EU/ml]; activation 287%;

Example 5

5 ml venous blood were collected from a patient diagnosed with testicular cancer and were processed as in Example 1.
The first step: $T_0=6.24$ s;
The second step: $T=3.12$ s; $A=1,00$ [EU/ml];
The third step:
$T_1=2.155$ s (1/100 dilution); $A_1=1.895$ [EU/ml]; activation 90%;
$T_2=1.553$ s (1/50 dilution); $A_2=3.018$ [EU/ml]; activation 202%;
$T_3=1.210$ s (1/10 dilution); $A_3=4.156$ [EU/ml]; activation 316%;

Example 6

5 ml venous blood were collected from a patient diagnosed with prostata cancer and were processed as in Example 1.
The first step: $T_0=6.42$ s;
The second step: $T=3.21$ s; $A=1,00$ [EU/ml];
The third step:
$T_1=2.407$ s (1/100 dilution); $A_1=1.708$ [EU/ml]; activation 71%;
$T_2=1.798$ s (1/50 dilution); $A_2=2.626$ [EU/ml]; activation 163%;
$T_3=1.475$ s(1/10 dilution); $A_3=3.418$ [EU/ml]; activation 242%;

Example 7

5 ml venous blood were collected from a patient diagnosed with leukemia and were processed as in Example 1.
The first step: $T_0=6.36$ s;
The second step: $T=3.18$ s; $A=1,00$ [EU/ml];
The third step:
$T_1=2.108$ s (1/100 dilution); $A_1=2.016$ [EU/ml]; activation 102%;
$T_2=1.279$ s (1/50 dilution); $A_2=3.610$ [EU/ml]; activation 261%;
$T_3=1.046$ s (1/10 dilution); $A_3=5.080$ [EU/ml]; activation 408%;

Example 8

5 ml venous blood were collected from a patient diagnosed with healthy volunteer and were processed as in Example 1.
The first step: $T_0=6.28$ s;
The second step: $T=3.14$ s; $A=1,00$ [EU/ml];
The third step:
$T_1=3.14$ s (1/100 dilution); $A_1=1.00$ [EU/ml]; activation 0%;
$T_2=3.09$ s (1/50 dilution); $A_2=1.032$ [EU/ml]; activation 3%;
$T_3=3.06$ s (1/10 dilution); $A_3=1.051$ [EU/ml]; activation 5%;

Example 9

The rapid method of carcinoma diagnosis according to the invention of the present application was tested on two groups of patients as follows:
Group 1 (N=2320): patients suffering from different types of carcinoma said carcinomas being histologically confirmed.
Group 2 (N=2638): healthy volunteers and patients having other diseases but not cancer.
In both groups venous blood was collected and the effect of serum at 1/100, 1/50 and 1/10 dilutions on purified carbonic anhydrase II was determined according to Example 1.

The results are presented in the table shown below, the values being mean values of the serum activating effect on purified carbonic anhydrase II.

| | | Carbonic anhydrase II + serum | | |
|---|---|---|---|---|
| Group | Diagnose | 1/100 | 1/50 | 1/10 |
| 1 | Carcinoma patients | 156% | 242% | 483% |
| 2 | Non-cancer patients | 0% | 4% | 9% |

The results show that purified carbonic anhydrase II is explosively activated by the serum of carcinoma patients and that the CA II activity is neither altered by the serum of healthy volunteers nor by the serum of non-cancer patients.

From the above results it is clear that the activating effect increases proportional to the serum concentration, i.e., in the Examples the maximum activating effect being obtained at 1/10 dilution (≈5 vol. % serum in the first reaction mixture), and the decrease of serum dilution (from 1/10 to 1/100 ) from 5 vol % to 0.5 vol. %) on the other hand reduces the activating effect of serum. Nevertheless the activating effect is obvious even at 1/100 dilution (≈0.5 vol. % serum in the first reaction mixture).

Utility

The method of the present invention provides a rapid test for diagnosis of different types of cancer.

The studies performed by applicants so far include over 3,000 patients, with different stage and localization of tumor processes including: pharyngeal cancer, gastric cancer, esophageal cancer, colorectal cancer, hepatocellular cancer, pancreatic, pulmonary, brest, ovarian, uterine cancer, testicular, prostate cancer, vesica urinary cancer, thyroidian, lips cancer, leukemia, malignant melanomas, Hodgkin lymphoma, etc.

Applicants described many categories of carbonic anhydrase activators and inhibitors which can be administered as therapeutic agents in different diseases and which could influence the test method described in the application. For this reason, it is strongly recommended to interrupt any treatment with $H_2$-receptor antagonists 5 days before performing the method for cancer diagnosis and also to interrupt any treatment with carbonic anhydrase inhibitors (acetazolamide, $E_1, E_2, I_2$ prostaglandins) or any non-steroidal anti-inflammatory drug treatment 10 days before performing the test.

Applicants' studies prove that the method of the present application can be used as a screening test for all types of cancer.

What is claimed is:

1. A method for cancer diagnosis in a subject to be tested, the method comprising
   (a) preparing a first reaction mixture by combining a diluted blood serum sample of the subject to be tested and a solution of purified carbonic anhydrase II;
   (b) preparing a second reaction mixture by combining all constituents of the first reaction mixture except the blood serum sample;
   (c) determining the activity of carbonic anhydrase II in the first reaction mixture;
   (d) determining the activity of carbonic anhydrase II in the second reaction mixture; and
   (e) assessing the degree of activation of carbonic anhydrase II in step (c) relative to step (d).

2. The method of claim 1, wherein the diluted blood serum sample contains from 0.1 to 50 vol. % of blood serum.

3. The method of claim 1, wherein the diluent of the diluted blood serum sample is at least one of a group consisting of water, an aqueous organic solvent and a buffer.

4. The method of claim 1, wherein the solution of purified carbonic anhydrase II comprises a concentration of carbonic anhydrase II that ranges from 0.01 nM to 1.0 mM, and the solvent of said solution is at least one from the group consisting of water, aqueous organic solvents, a buffer and an indicator.

5. The method of claim 1, wherein the diluted blood serum sample and the solution of purified carbonic anhydrase are combined at a ratio of 100:1 to 1:100.

6. The method of claim 1, wherein the first reaction mixture contains from 0.05 to 25 vol. % of blood serum.

7. The method of claim 6, wherein a carbonic anhydrase II activity of 100% or higher in the first reaction mixture relative to the carbonic anhydrase II activity of the second reaction mixture indicates the presence of a carcinogenic process in the subject.

8. The method of claim 1, wherein the diluted blood serum sample is an aqueous solution containing 10 vol. % serum, the solution of purified anhydrase II is an aqueous buffer solution containing from 1.0 to 10 nM carbonic anhydrase II and the first reaction mixture is prepared by combining the diluted blood serum sample and the solution of purified carbonic anhydrase II at a ratio of 1:1.

9. The method of claim 1, wherein the determination of the carbonic anhydrase II activity in steps (c) and (d) of claim 17 is performed by a stop-flow kinetic measuring the $CO_2$ hydration of said enzyme.

10. The method of claim 9, wherein the initial pH of the first and second reaction mixtures is about 7.5, and wherein the determination of the activity of carbonic anhydrase II comprises
    (a) adding a substrate solution to the first and to the second reaction mixtures, the substrate solution comprising an aqueous solution containing from 5 to 50 mM $CO_2$; and
    (b) measuring the time until the final pH of 6.5 is reached.

11. The method of claim 1 wherein the subject to be tested is suspected to have a cancer in any stage of the cancer process.

12. The method of claim 11, wherein the subject to be tested is suspected to have a cancer in a stage selected from the group comprising the asymptomatic phase and an early stage.

13. The method of claim 1, wherein the subject to be tested is suspected of having a condition selected from the group consisting of pharyngeal, gastric, esophageal, colorectal, hepatocellular, pancreatic, pulmonary, breast, ovarian, uterine, testicular, prostatic, vesica urinary, thyroidian and lip cancer, leukemia, malignant melanomas and Hodgkin lymphoma.

14. A kit for performing the method for cancer diagnosis of claim 1, comprising carbonic anhydrase II in a container and instructions for carrying out the method of claim 17.

15. A kit according to claim 14 further comprising a composition comprising at least one said tumor marker activating carbonic anhydrase II at concentrations of 1 $\mu$M or below.

16. The kit according to claim 15, wherein the tumor marker is selected from the group consisting of tumor necrosis factor $\alpha$, tumor necrosis factor $\beta$, carcinoembryonic antigen, sialic acid, $\alpha$,—antichymothrypsine and sp $185^{Her2}$ oncoprotein.

* * * * *

UNITED STATES PATENT AND TRADEMARK OFFICE
CERTIFICATE OF CORRECTION

PATENT NO.    : 6,326,161 B1
DATED         : December 4, 2001
INVENTOR(S)   : Ioan Puscas et al.

It is certified that error appears in the above-identified patent and that said Letters Patent is hereby corrected as shown below:

<u>Title page, Item [54] and Column 1, line 1,</u>
"RAPID MOTOR FOR CANCER DIAGNOSIS" is changed to -- RAPID METHOD FOR CANCER DIAGNOSIS --

Signed and Sealed this

Fourth Day of June, 2002

*Attest:*

*Attesting Officer*

JAMES E. ROGAN
*Director of the United States Patent and Trademark Office*